United States Patent [19]

MacIntyre

[11] Patent Number: 5,438,982

[45] Date of Patent: Aug. 8, 1995

[54] ENDOTRACHEAL TUBE ADAPTED FOR AEROSOL GENERATION AT DISTAL END THEREOF

[76] Inventor: Neil R. MacIntyre, 3920 Wentworth Dr., Durham, N.C. 27707

[21] Appl. No.: 139,636

[22] Filed: Oct. 19, 1993

Related U.S. Application Data

[63] Continuation of Ser. No. 849,168, Mar. 10, 1992, abandoned.

[51] Int. Cl.6 .................... A61M 11/00; A61M 16/10; A61M 15/00; A62B 9/06
[52] U.S. Cl. ..................... 128/207.14; 128/203.12; 128/200.14
[58] Field of Search .............. 128/200.14, 203.12, 128/207.14, 207.15, 911, 912

[56] References Cited

U.S. PATENT DOCUMENTS

| | | | |
|---|---|---|---|
| 4,327,721 | 5/1982 | Goldin et al. | 128/207.15 |
| 4,425,914 | 1/1984 | Ray et al. | 128/207.15 |
| 4,584,998 | 4/1986 | McGrail | 128/207.15 |
| 4,739,756 | 4/1988 | Horn | 128/207.15 |
| 4,821,714 | 4/1989 | Smelser | 128/207.15 |
| 4,955,375 | 9/1990 | Martinez | 128/207.15 |
| 4,977,894 | 12/1990 | Davies | 128/207.15 |
| 5,031,613 | 7/1991 | Smith et al. | 128/207.15 |
| 5,088,486 | 2/1992 | Jinotti | 128/207.14 |

FOREIGN PATENT DOCUMENTS

| | | |
|---|---|---|
| 112668 | 7/1984 | European Pat. Off. . |
| 0245142 | 11/1987 | European Pat. Off. ....... 128/207.14 |
| 245142 | 11/1987 | European Pat. Off. . |
| 436353 | 7/1991 | European Pat. Off. . |
| 9106933 | 10/1991 | Germany . |
| 2033759 | 5/1980 | United Kingdom . |

*Primary Examiner*—Kimberly L. Asher
*Attorney, Agent, or Firm*—Richard E. Jenkins

[57] ABSTRACT

An endotracheal tube adapted for aerosol generation at the distal end thereof and which is a modification of existing endotracheal tubes. The improved tube incorporates first and second conduits along the length thereof in order to deliver a liquid to be aerosolized and a high velocity gas at the distal end of the endotracheal tube so as to create an aerosol within the lungs. The distal end of the gas conveying catheter is configured to direct the high velocity gas transported therethrough across the pathway of the liquid solution exiting the distal end of the first conduit to facilitate the creation of an aerosol for high efficiency delivery of the liquid solution.

34 Claims, 3 Drawing Sheets

ENDOTRACHEAL TUBE ADAPTED FOR AEROSOL GENERATION AT DISTAL END THEREOF

This is a continuation of application Ser. No. 07/849,168 filed on Mar. 10, 1992, now abandoned.

TECHNICAL FIELD

The present invention relates generally to endotracheal tubes, and more particularly to an endotracheal tube designed to allow for the generation of an aerosol at the distal end thereof for direct delivery to the lungs.

RELATED ART

Aerosol delivery to the lungs is an important therapeutic modality in respiratory medicine. Through aerosols a variety of solutions can be delivered directly to the lung tissue for various purposes such as to dilate airways, treat infections and to replace surfactant. Conventional aerosol generators are of the "jet" variety wherein a jet of gas is placed over the solution to be aerosolized and particles of about 1.0–5.0 micrometers are created. Unfortunately, actual lung delivery of aerosolized solutions from these devices is quite low. As is well known to those skilled in the art, even with the best of technique, standard aerosolization devices (nebulizers) with appropriate mouthpieces deliver only about 5.0–20.0% of their material into the lungs, and the remainder is wasted in the mouth or exhaled back out into the environment.

The inadequacies of conventional aerosol delivery to the lungs is made even worse when an endotracheal tube is placed into a patient's airway and connected to a mechanical ventilator at the proximal end thereof. Once this procedure is accomplished, aerosol delivery through the tube (which is typically about 6.0–10.0 millimeters in diameter and about 30.0 centimeters long) is reduced to less than 5% since the tube is narrow and bent and many times is partially filled with mucus or other respiratory secretions. All of the circumstances serve as a significant barrier to aerosol delivery into the lungs when a patient has been intubated with an endotracheal tube. Therefore, it is a common practice to substantially increase the solution dose being applied by a nebulizer to an endotracheal tube to compensate for the fact that the endotracheal tube will limit aerosol delivery and deposition within the lungs. Thus, there is a long-felt need for a device which will provide for increased aerosol delivery to mechanically ventilated patients with endotracheal tubes (intubated patients) since such a device would provide higher efficacy of aerosol delivery and would be very cost effective in use.

A number of attempts have been made to overcome the shortcomings inherent in the use of conventional nebulizers to deliver an aerosol through an endotracheal tube to the lungs of a mechanically ventilated patient. The most common approach to the problem is the aforementioned increase in the aerosolized solution in order to compensate for the fact that 90–95% of the solution will not actually be introduced into the lungs. Also, metered dose inhalers of the type which generate aerosols from pressurized canisters have been advocated for use. However, since these devices generate similar aerosol particle characteristics, these devices also have shown only nominal improvement in lung deposition of the aerosolized solution.

A variety of techniques placing the nebulizer at different points in the ventilator circuitry have also proved to be of only minimal benefit. In further efforts to overcome the shortcomings of conventional aerosol delivery to the lungs of an intubated patient, catheters have been developed to deliver aerosols which are generated at the proximal end of the endotracheal tube and delivered at the distal end thereof. Unfortunately, as is well known to those skilled in this art, these catheters usually cause the aerosol particles introduced at the proximal end to coalesce during the passage to the distal end and the aerosolized solution thus tends to drip from the distal end. Consequently, delivery of the solution to lung tissue beyond the airways is substantially defeated by this phenomenon.

Therefore, the search continues for an endotracheal tube which is capable of delivering an aerosolized solution with a high degree of efficacy into the lungs of an intubated patient.

DISCLOSURE OF THE INVENTION

The present invention comprises an endotracheal tube for aerosol delivery of a selected liquid solution to the lungs. The tube comprises a tubular member for ventilating a patient which has a distal end for insertion into the trachea and a proximal end adapted for introduction of a breathable gas. A first conduit is provided for delivery of a selected liquid solution to the lungs and has a proximal end terminating adjacent the proximal end of the tubular member and a distal end terminating adjacent the distal end of the tubular member. A second conduit is provided for high velocity delivery of a gas and has a proximal end terminating adjacent the proximal end of said tubular member and a distal end terminating adjacent the distal end of the tubular member. The distal end of the second conduit is configured so as to direct the high velocity gas flow across the pathway of the liquid solution exiting the distal end of the first conduit so as to create an aerosol. Most suitably both the first and second conduits are embedded adjacent each other in the wall of the tubular member and are positioned inwardly from the distal end thereof a distance of between about 1.0–2.0 centimeters.

It is therefore the object of this invention to provide an improved endotracheal tube which eliminates the problems described above.

More specifically, it is the object of the present invention to provide an endotracheal tube which generates a jet aerosol at the distal end thereof so as to assure high efficiency aerosol delivery of a desired medication to the lungs.

It is yet another object of the present invention to provide an endotracheal tube which provides enhanced aerosol delivery of a selected medication to the lungs so as to reduce the amount of medication needed for the treatment.

Some of the objects of the invention having been stated, other objects will become evident as the description proceeds, when taken in connection with the accompanying drawings described below.

BEST MODE FOR CARRYING OUT THE INVENTION

The invention described herein is a modification of a commonly used medical device called an endotracheal tube which possesses significant advantages thereover by providing the ability to generate an aerosol at the distal end thereof for enhanced delivery of a medication to the lungs.

Figure 1:
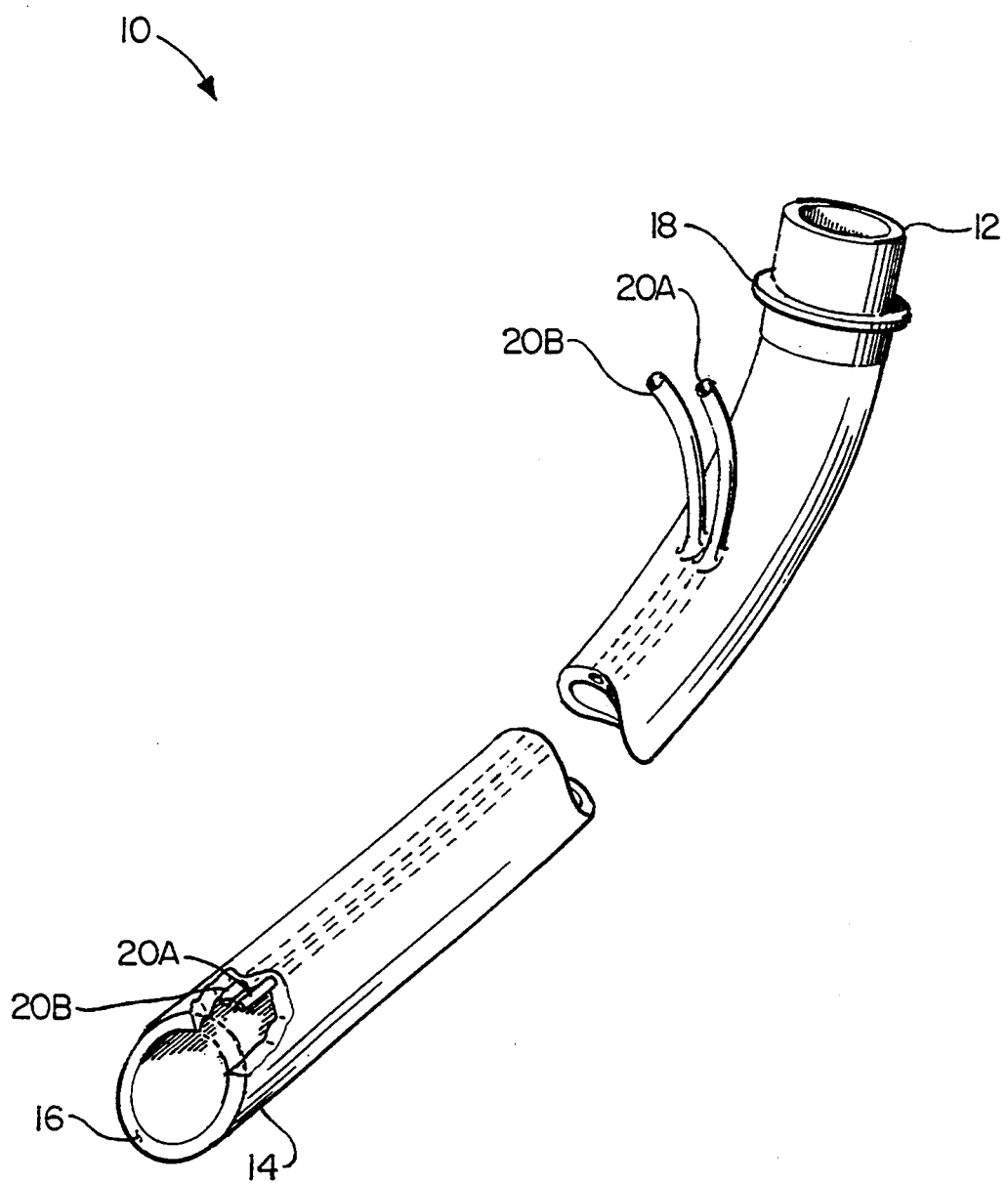
FIG. 1 is a perspective view, with parts broken away for clarity, of an endotracheal tube incorporating a preferred embodiment of the invention.
Figure 2:
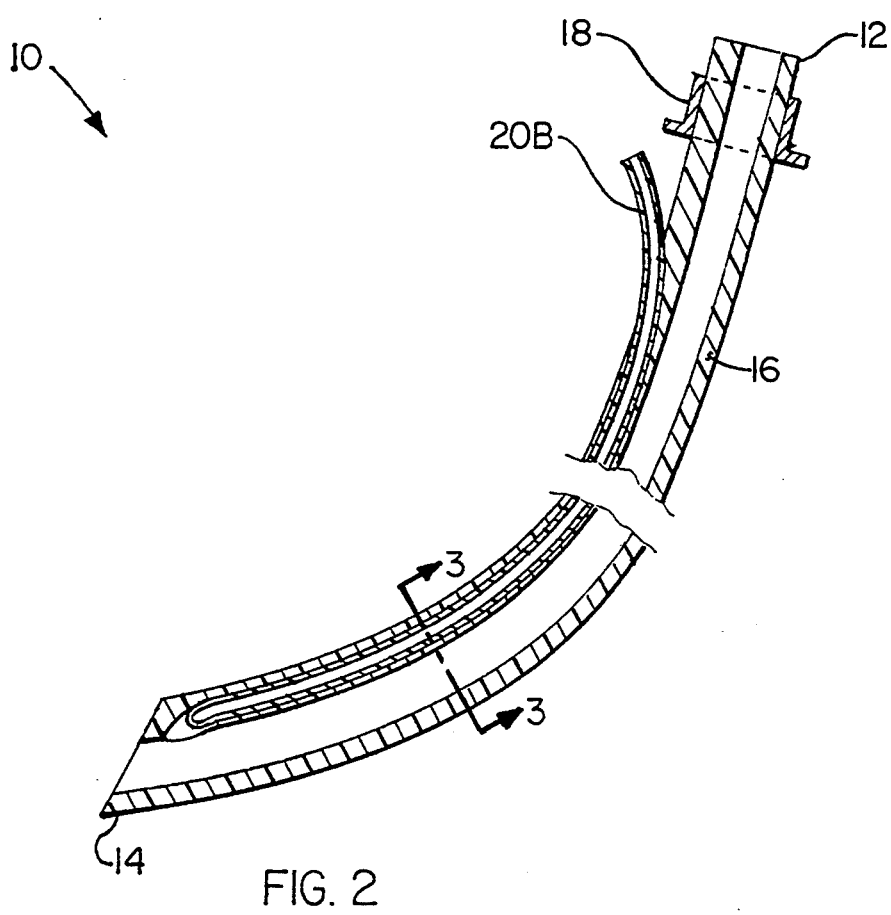
FIG. 2 is a vertical cross-sectional view taken along line 2—2 of FIG. 3.
Figure 3:
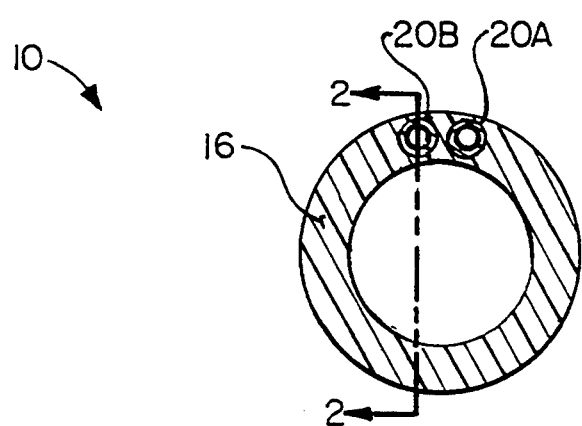
FIG. 3 is a horizontal cross sectional view taken along line 3—3 of FIG. 2.
Figure 4:
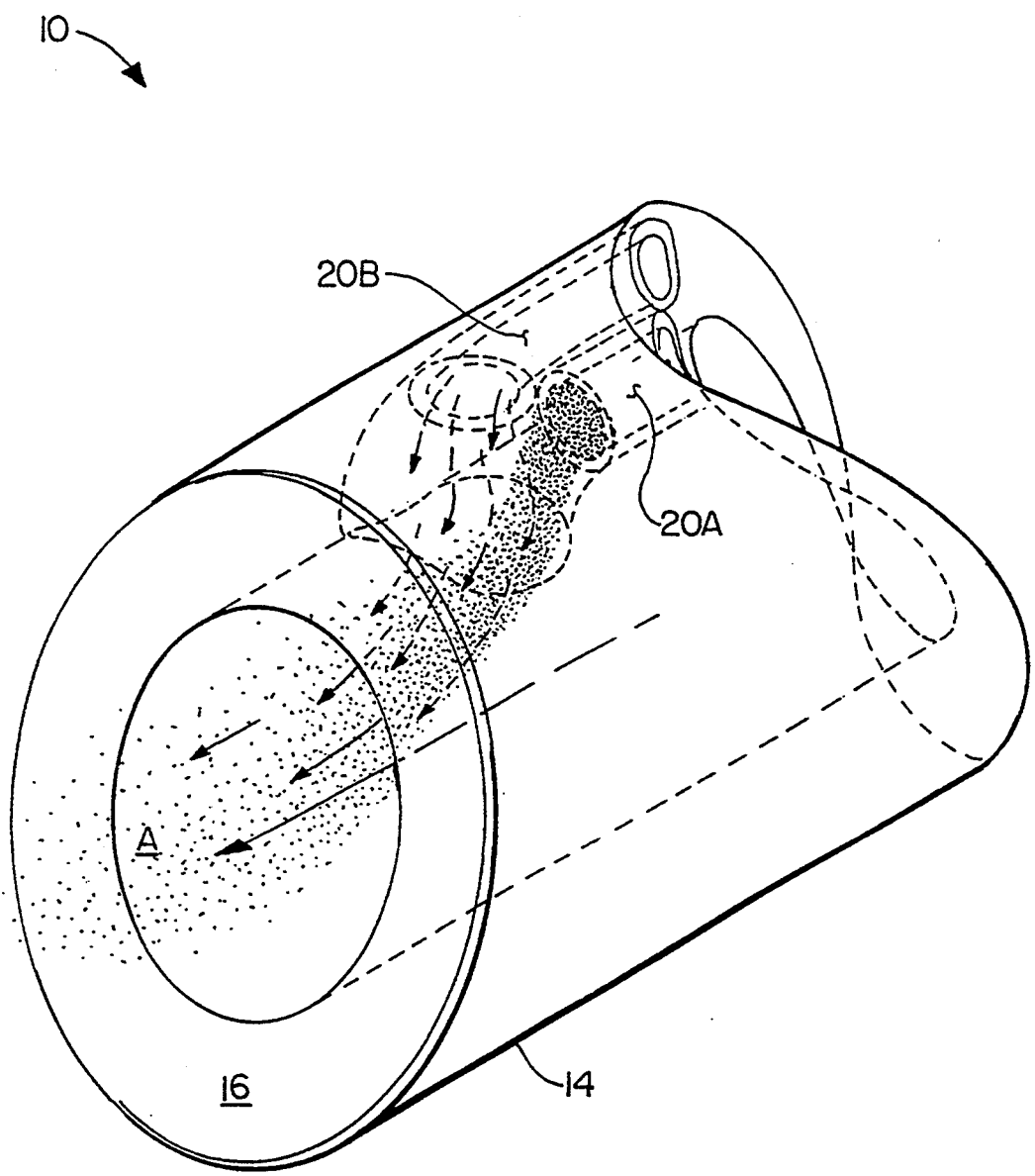
FIG. 4 is an enlarged fragmentary view of the distal end of the endotracheal tube shown in FIG. 1.

Referring to FIGS. 1–4, an endotracheal tube 10 in accordance with the present invention is shown having a proximal end 12, a distal end 14, and a side wall 16 (see FIGS. 2–4). The proximal end 12 typically includes a conventional coupling device 18 for attachment to ventilating equipment or other medical equipment as known to those skilled in this art. Endotracheal tube 10 of the present invention may most suitably be extruded from polyvinyl chloride or other suitable flexible plastic-type material.

Endotracheal tube 10 includes two side-by-side small diameter catheters, 20A, 20B, which are embedded in wall 16 of the tubular member. Small diameter catheters 20A, 20B, extend adjacent each other substantially along the length of endotracheal tube 10 in embedded relationship to side wall 16 (see FIGS. 2–4). The proximal ends of catheters 20A, 20B, extend outwardly and are spaced apart from wall 16 adjacent proximal end 12 of endotracheal tube 10 (see FIG. 1) and, most suitably, the distal ends thereof terminate about 1.0–2.0 centimeters short of distal end 14 of endotracheal tube 10 and in fluid communication with the internal passageway thereof (see FIG. 4). Although the preferred embodiment shown in FIGS. 1–4 of the drawings depicts catheters 20A, 20B as embedded within wall 16 of endotracheal tube 10, applicant contemplates that suitable first and second lumens could also be incorporated in wall 16 of the tube during the manufacturing process and suitable proximal and distal ends fitted to both lumens as an alternative to the two small diameter catheters 20A, 20B provided in the preferred embodiment shown herein.

In use, a desired aerosol medication solution would be mixed and placed into a bag so that the solution could be pumped through fluid catheter 20A at a constant rate selected by a clinician. Catheter 20B would be attached to a gas source so as to provide a suitable high velocity gas such as at the distal end thereof. As best seen in FIG. 4 of the drawings, the distal end of the gas-conveying small catheter 20B is formed with an exit aperture formed so as to direct the gas across the pathway of the liquid exiting from small diameter catheter 20A and to produce an aerosol A (see FIG. 4) in the trachea at the entrance to the lungs. The distal ends of both catheters 20A and 20B are most suitably formed so as to be in fluid communication with the internal passageway of endotracheal tube 10 at or near the distal end thereof. By producing the aerosol at this location as opposed to previously known techniques of introducing an aerosol at the proximal end of an endotracheal catheter, a virtual 100% efficiency of delivery of the desired medication aerosol solution to the lungs is assured and the amount of medication needed for a given treatment is significantly reduced from what is normally utilized.

In order to prevent lung injury from the high velocity gas flow from catheter 20B, the distal ends of catheters 20A, 20B, are most suitably about 1.0–2.0 centimeters short of distal end 14 of the endotracheal tube although other configurations of catheters 20A, 20B for producing aerosol A at distal end 14 of tube 10 are contemplated as within the scope of applicant's invention. In order to optimize performance of endotracheal tube 10, one skilled in the art would need to suitably adjust gas flow from catheter 20B, fluid flow from catheter 20A, the diameters of catheters 20A, 20B and the angle of intersection of the gas emitted by the distal end of catheter 20B with the liquid emitted at the distal end of catheter 20A in order to provide an aerosol particle size of about 1.0–5.0 micrometers. Also, in view of the reduced use of medication resulting from use of applicant's inventive endotracheal tube 10, appropriate dosing adjustments would have to be made by clinicians during use thereof.

It will be understood that various details of the invention may be changed without departing from the scope of the invention. Furthermore, the foregoing description is for the purpose of illustration only, and not for the purpose of limitation—the invention being defined by the claims.

What is claimed is:

1. An endotracheal tube for aerosol delivery of a selected liquid solution to the lungs comprising:

a tubular member for ventilating a patient comprising a distal end for insertion into the trachea of a patient and a proximal end adapted for introduction of a breathable gas into said tubular member;

a first conduit for delivery of a selected liquid solution to the lungs having a proximal end terminating adjacent the proximal end of said tubular member and a distal end terminating adjacent the distal end of said tubular member, said first conduit extending substantially along the length of said tubular member; and a second conduit for high velocity delivery of a gas having a proximal end terminating adjacent the proximal end of said tubular member and a distal end terminating adjacent the distal end of said tubular member, said second conduit extending substantially along the length of said tubular member, said second conduit comprising means for directing high velocity gas across a liquid solution exiting the distal end of said first conduit and thereby creating an aerosol.

2. An endotracheal tube according to claim 1 wherein said first and second conduits are embedded within the wall of said tubular member.

3. An endotracheal tube according to claim 2 wherein said first and second conduits are positioned adjacent each other within the wall of said tubular member.

4. An endotracheal tube according to claim 1 wherein said first and second conduits terminate between about 1.0–2.0 centimeters before the distal end of said tubular member and in fluid communication with the internal passageway defined by said tubular member.

5. An endotracheal tube according to claim 1 wherein said endotracheal tube creates an aerosol at the distal end thereof having a particle size between about 1.0–5.0 micrometers.

6. The endotracheal tube of claim 1 wherein said directing means comprises:

an exit aperture of said second conduit oriented relative to said pathway to nebulize said liquid solution.

7. The endotracheal tube of claim 1 wherein said directing means comprises:
the distal end of said second conduit being less than 2 centimeters from the distal end of the first conduit.

8. The endotracheal tube of claim 1 wherein said directing means comprises:
an exit aperture of said second conduit being angled toward the pathway.

9. The endotracheal tube of claim 8 wherein the exit aperture is obliquely angled toward the pathway.

10. An endotracheal tube for aerosol delivery of a selected liquid solution to the lungs comprising:
a tubular member for ventilating a patient comprising a distal end for insertion into the trachea of a patient and a proximal end adapted for introduction of a breathable gas into said tubular member;
a first conduit for delivery of a selected liquid solution to the lungs having a proximal end terminating adjacent the proximal end of said tubular member and a distal end terminating adjacent the distal end of said tubular member, said first conduit extending substantially along the length of said tubular member and being embedded within the wall thereof; and
a second conduit embedded within the wall of said tubular member adjacent said first conduit for high velocity delivery of a gas and having a proximal end terminating adjustment the proximal end of said tubular member and a distal end terminating adjacent the distal end of said tubular member, said second conduit extending substantially along the length of said tubular member and the distal end thereof being less than 2 centimeters from the distal end of the first conduit and having a configuration that directs high velocity gas across a liquid solution exiting the distal end of said first conduit and therefor creating an aerosol.

11. An endotracheal tube according to claim 10 wherein said first and second conduits terminate between about 1.0–2.0 centimeters before the distal end of said tubular member and in fluid communication with the internal passageway defined by said tubular member.

12. An endotracheal tube according to claim 10 wherein said endotracheal tube creates an aerosol at the distal end thereof having a particle size between about 1.0–5.0 micrometers.

13. A method for efficient aerosol delivery of a selected liquid medicine solution to the lungs of an intubated patient comprising:
(a) inserting an endotracheal-type tube into the trachea of a patient wherein said tube comprises a distal end for insertion into the trachea and a proximal end for introduction of a breathable gas into said tube, said tube further comprising relatively smaller diameter first and second conduits having particular configurations and extending substantially along the length of said tube, wherein each of said first and second conduits comprises a proximal end and a distal end generally corresponding to the proximal and distal ends of said tube and the distal ends of said first and second conduits are in fluid communication with the interior of the distal end of said tube;

(b) delivering a selected liquid medication solution to the lungs by introducing the liquid into the distal end of said tube by said first conduit; and
(c) delivering a high velocity gas to the distal end of said tube by said second conduit and angling the gas across the pathway of the liquid medicine solution via the configurations of the first and second conduits so as to create an aerosol.

14. The method of claim 13 in which the aerosol is directed into the interior of said tube.

15. The method of claim 13 further comprising the step of: mixing the medication solution.

16. The method of claim 13 further comprising the step of:
pumping the medication solution through the first conduit.

17. The method of claim 16 in which the pumping step is at a constant rate.

18. The method of claim 13 further comprising the step of:
attaching a gas source to the proximal end of the second conduit.

19. The method of claim 13 further comprising the step of:
producing an aerosol in the trachea.

20. The method of claim 13 in which the aerosol solution has a virtual 100% efficiency of delivery.

21. The method of claim 13 in which the delivery step is further characterized as producing an aerosol of the liquid medication having a particle size of about 1.0 to 5.0 micrometers.

22. In combination:
an endotracheal tube for ventilating a patient, said endotracheal tube having:
a proximal end, a distal end, and a tubular member extending therebetween, said tubular member comprised of a wall defining an internal passageway therethrough;
a first lumen for delivery of a liquid medicine, said first lumen extending from adjacent the proximal end to adjacent the distal end, said first lumen communicating with a first distal exit aperture located close to the distal end; and
a second lumen for delivery of a gas, said second lumen extending from adjacent the proximal end to adjacent the distal end, said second lumen communicating with a second distal exit aperture located close to the distal end, said second exit aperture oriented relative to the first exit aperture and having a configuration that directs a flow of gas exiting from the second exit aperture across liquid medicine exiting the first exit aperture, whereby liquid medicine delivered through the first exit aperture is aerosolized.

23. The invention of claim 22 wherein the first lumen and the second lumen communicate with the internal passageway.

24. The invention of claim 22 in which the first exit aperture and the second exit aperture are substantially adjacent to each other.

25. The invention of claim 22 in which the first exit aperture and the second exit aperture are less than 2 centimeters apart.

26. The invention of claim 22 in which the first exit aperture and the second exit aperture are less than 1 centimeter apart.

27. The invention of claim 22 in which the first exit aperture and the second exit aperture are less than 2 centimeters from a distal end of the endotracheal tube.

28. The invention of claim 22 in which the first exit aperture and the second exit aperture are less than 1 centimeter from the distal end of the endotracheal tube.

29. The invention of claim 22 wherein said first lumen is located in a first catheter.

30. The invention of claim 29 wherein said second lumen is located in a second catheter.

31. The invention of claim 22 in which said first lumen is located in a first catheter and said second lumen is located in a second catheter and further wherein said first catheter and said second catheter are side-by-side.

32. The invention of claim 31 wherein said first catheter and said second catheter are embedded in said wall.

33. The invention of claim 22 wherein said first lumen is incorporated in said wall.

34. The invention of claim 22 wherein said second lumen is incorporated in said wall.

* * * * *